United States Patent [19]
Chevallet et al.

[11] Patent Number: 5,047,147
[45] Date of Patent: Sep. 10, 1991

[54] SINGLE-NEEDLE ARTIFICIAL KIDNEYS

[75] Inventors: Jacques Chevallet, Serezin du Rhone; Olivier Roy, Annemasse, both of France

[73] Assignee: Hospal Industrie, Cedex, France

[21] Appl. No.: 276,091

[22] Filed: Nov. 23, 1988

Related U.S. Application Data

[63] Continuation of Ser. No. 672,666, Nov. 19, 1984, abandoned.

[51] Int. Cl.$^5$ .............................................. B01D 61/32
[52] U.S. Cl. .................................... 210/101; 210/134; 210/321.6; 210/496.1
[58] Field of Search ...................... 604/4, 5, 6; 210/90, 210/101, 85, 134, 87, 416.1, 321.6, 321.7, 97

[56] References Cited

U.S. PATENT DOCUMENTS 4,275,726 6/1981 Schael .............................. 604/31 X
4,490,135 12/1984 Trouther ................................ 604/5

Primary Examiner—Frank Spear
Attorney, Agent, or Firm—Finnegan, Henderson, Farabow, Garrett & Dunner

[57] ABSTRACT

Artificial kidney of the single-needle type, incorporating an extracorporeal blood circuit provided with a haemodialyser (13) or haemofilter (31) positioned between two blood circulation pumps (12, 19). This circuit is also provided with a bubble trap (18) and a safety clamp (26) and means for perfusing quantities of liquid which are capable of being relatively large. The perfusing means comprise a reservoir (23) and a perfusion pump (24) the motion of which is under the control of the sequential motion of one of the two blood circulation pumps (12, 19) and also comprise a conduit connecting the reservoir (23) to the extracorporeal blood circuit by way of the perfusion pump (24).

9 Claims, 2 Drawing Sheets

SINGLE-NEEDLE ARTIFICIAL KIDNEYS

This is a continuation of application Ser. No. 672,666, filed Nov. 19, 1984, now abandoned.

DESCRIPTION

The present invention relates to artificial kidneys.

One known type of artificial kidney incorporates an extracorporeal blood circuit connected to the arterial-venous network of a patient by a single access, such as a needle or catheter which is Y- or T-shaped. The extracorporeal blood circuit includes means for the treatment of blood, particularly for purification of the blood by passing it over a semipermeable membrane, such as a haemodialyser and/or haemofilter, which is positioned between two blood circulation pumps, the arterial pump being situated upstream of the blood treatment device and the venous pump being situated downstream of this device.

Artificial kidneys of this type have the advantage, relative to the traditional kidneys which are connected to the patients by two independent needles, of only requiring a single access to the patient's arterial-venous network at each treatment, resulting in considerably less trauma.

The single-needle artificial kidneys having two pumps, an arterial and a venous pump, have an efficiency comparable with that of a conventional two-needle artificial kidney. Furthermore, they permit better control of the average blood pressure between the two pumps, thereby permitting better monitoring of the withdrawal of the ultrafiltrate.

However, a problem arises when it is necessary to remove from the patient relatively large quantities of ultrafiltrate, which must generally be compensated at once by perfusing substantially equivalent volumes of physiological liquid and/or sterile solutions, minus any volume which is the equivalent of any weight loss desired for the patient.

In effect, if these perfusions are performed according to a continuous flow, whether constant or variable, on account of the pulsed return of the blood to the patient, there is a risk of sending him back a blood/perfused solution mixture which has not yet been homogenised, and this can in certain cases cause physiological disturbances in the patient.

These disadvantages can be further aggravated by an unfavourable choice in the siting of the perfusion point in the extracorporeal circuit. On the one hand, if the perfusion point is situated upstream of the blood treatment apparatus, one part of the liquid perfused may be removed immediately by ultrafiltration and never reach the patient. On the other hand, if the perfusion is carried out downstream of the blood treatment apparatus, but at a point remote from the venous pump, there is the risk of sending back to the patient a blood/perfused solution mixture which is very heterogeneous, and this risk can be aggravated by the risk of recirculating a part of the perfused solution in the single-needle circuit, via the single needle and the arterial pump.

Moreover, in artificial kidneys equipped with devices for measuring and monitoring venous pressure, the perfusion of solutions can create pressure variations which are capable of triggering premature warning signals.

An object of the present invention is to propose a polyvalent artificial kidney which enables benefit to be drawn from the advantages of single-needle double-pump circuits, and also to perform treatments for cleansing the blood by haemodialysis and/or by ultrafiltration-reinjection at high rates.

Another object of the present invention is an artificial kidney permitting ultrafiltration-reinjection treatments which offer excellent assurances of regularity, reliability and safety from the physiological standpoint.

A further object of the present invention is an artificial kidney, the functioning of which is simple, economical, automatic, reliable and safe.

According to the present invention there is provided an artificial kidney comprising an extracorporeal blood circuit including:
(a) a blood treatment apparatus which contains a selectively permeable membrane;
(b) a single needle connectable to a patient's arterial-venous network;
(c) a first pump having an inlet port connected to said needle and an outlet port connected to said blood treatment apparatus;
(d) a second pump having an inlet port connected to said blood treatment apparatus and an outlet port connected to said needle;
(e) first and second actuating means for causing the operation of said first and second pumps, respectively;
(f) at least one reservoir for at least one solution to be introduced into said extracorporeal blood circuit;
(g) at least one perfusion pump having an inlet port connected to a respective reservoir and an outlet port connected to said extracorporeal blood circuit;
(h) third actuating means for causing the operation of said perfusion pump; and
(i) means connecting the third actuating means with one of the first and second actuating means, whereby the operation of the perfusion pump is controlled as a function of the operation of the respective one of said first and second pumps.

In order that the invention may more readily be understood, the following description is given, merely by way of example, reference being made to the accompanying drawings, in which.

For greater simplicity, like parts shown in the various Figures are designated by like reference numerals.

Figure 1:
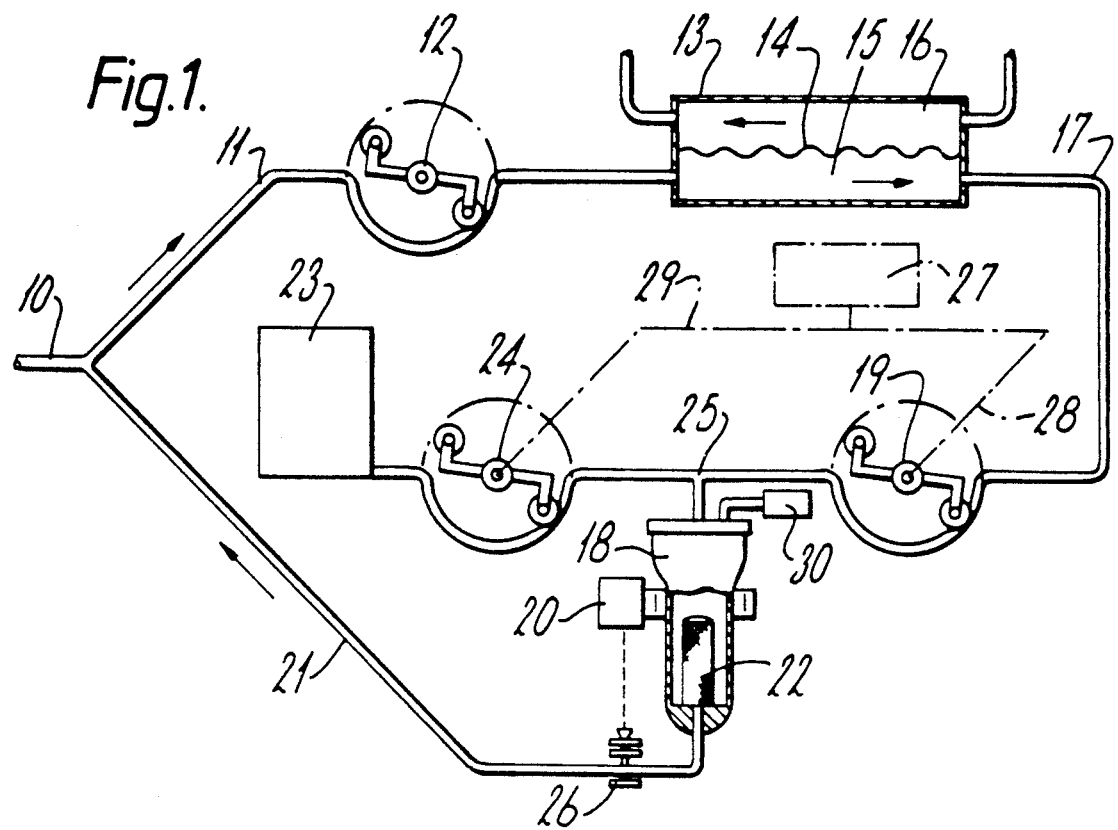
FIG. 1 is a schematic view of a first embodiment of artificial kidney according to the invention.

Referring first to FIG. 1, it can be seen that the blood is withdrawn from the patient by means of a single access of any type known per se, such as a needle or a catheter, which is Y- or T-shaped. The blood travels through an extracorporeal circuit composed essentially of a treatment apparatus provided with a selectively permeable membrane, such as a haemodialyser and/or haemofilter, circulation pumps, various accessories of which only the main ones are shown, and connecting lines between these various devices.

Thus, in the line 11, which generally consists of a flexible polyvinyl chloride tube, the blood is drawn by means of a first pump 12, for example of the peristaltic type, from the needle 10 to a haemodialyser 13. This first pump 12, which feeds the haemodialyser and is situated upstream of the latter, conveys the blood which is originally at the arterial pressure of the patient and can for this reason be called the "arterial pump". The haemodialyser 13, of any type known per se, essentially comprises a membrane 14 which permits dialysis and ultrafiltration of the blood, the membrane dividing the haemodialyser into two compartments 15 and 16, the first compartment being passed through by the blood and the second by the dialysis liquid which can also carry the ultrafiltrate with it.

A line 17, of similar type to the line 11, carries the blood from the haemodialyser 13 to a bubble-remover 18 of any type known per se, by means of a second pump 19, which is arranged downstream of the haemodialyser, and delivers the treated blood to the patient at the patient's venous pressure; this pump can for this reason be called the "venous pump" and is preferably of similar, or even identical, type to the arterial pump 12.

The bubble-remover 18 has the essential function of holding back any air bubble which might run the risk of being carried along by the blood to the patient in the extra-corporeal circuit. The presence of air bubbles, or foam consisting of a conglomeration of very fine air bubbles, is detected by a device 20 which has priority control over the automatic closing of an obstructing clamp 26, of any known type, which is situated on a line 21 directly connecting the bubble-remover 18 to the single-needle device 10. The operation of the clamp 26 is also advantageously synchronised with the operation of the venous pump 19, that is to say the clamp is open when the pump 19 rotates. Preferably, a filter 22 situated at the bottom of the bubble-remover 18, holds back impurities, dust or haemolysed cells before returning the blood to the patient. Furthermore, a device 30 is generally provided for measuring the blood pressure at any point of the return circuit between the pump 19 and the needle 10, preferably between the pump 19 and the clamp 26, and advantageously for example, on the bubble-remover 18.

The clamp 26 is generally situated, on the one hand upstream of the single needle 10, and on the other hand downstream of any other member present in the return circuit of the blood to the patient. This permits a considerable limitation in the risks of a leakage of blood or inopportune entry of air, for example at a simple tubing connector which might be defective. Naturally the pressure measuring device 30 can be situated without disadvantage downstream of the clamp 26, since it is arranged around the line 21 and is only in contact with the external wall of this line, no specific connector being required.

The operation of this type of artificial kidney is sequential, the blood travelling through the single needle 10 alternately from the patient to the haemodialyser 13 and then from the latter to the patient. The blood-circulating pumps 12 and 19 therefore generally operate discontinuously and out-of-phase. The regulation is accomplished either by programming the respective operating periods, or preferably in relation to the blood pressure between the two pumps, to avoid any excessive pressure difference. Generally, an abnormal pressure detected by the device 30 causes the arrest of the venous pump 19.

All components of the artificial kidney described hitherto are well known and therefore will not be described here in further detail.

According to the present invention, means are provided which enable relatively large quantities of ultrafiltrate, for example of the order of 3 to 4 liters per session, or even more, to be withdrawn from a patient who is enjoying the advantages of a treatment by a single-needle artificial kidney having double circulation pumps, and to compensate these quantities, except in respect of any weight loss desired for the patient, by perfusions of substantially equivalent volumes of physiological solutions which are generally isotonic with the blood.

These means of perfusion consist of a reservoir 23, of any type known and of the desired capacity, connected to a perfusion pump 24, for example an occlusive peristaltic pump; the latter is connected to the extracorporeal blood circuit by a perfusion conduit, at a perfusion point 25. The means of actuating the perfusion pump are under the control of the means of actuating one of the two blood-circulating pumps, generally that which is closest to the perfusion point. They are preferably synchronised with each other, that is to say they operate and stop simultaneously with each other. It has been observed that it is possible in this way to cause the blood and the perfusion liquid to arrive simultaneously at the perfusion point, in a predetermined ratio of flow rates which can advantageously be adjusted. It has also been observed that downstream of the perfusion point, the blood and perfusion liquid mix in a substantially homogeneous manner and in approximately constant proportions, and that this mixture can be injected into the patient without causing physiological disturbances.

The device 27 is shown schematically as a control member of any known type, for example provided with a programmer which acts, electrically or electronically for example, via lines 28 and 29, on the respective motors of the pumps 19 and 24.

According to the invention, it has been found advantageous to situate the injection point in the extracorporeal blood circuit in proximity to the inlet or outlet port of the circulation pump whose means of actuation control the means of actuation of the perfusion pump. The expression "in proximity to", means that there is no significant member, such as a bubble-remover, pulsation-absorbing device or valve, capable of modifying the desired proportioning of perfusion liquid relative to the blood, interposed between the perfusion pump and the injection point, the distance between these two components being of secondary importance since it is generally small. Thus, on FIG. 1, the injection point 25 is shown situated close to, and downstream of, the venous pump 19.

Figure 2:
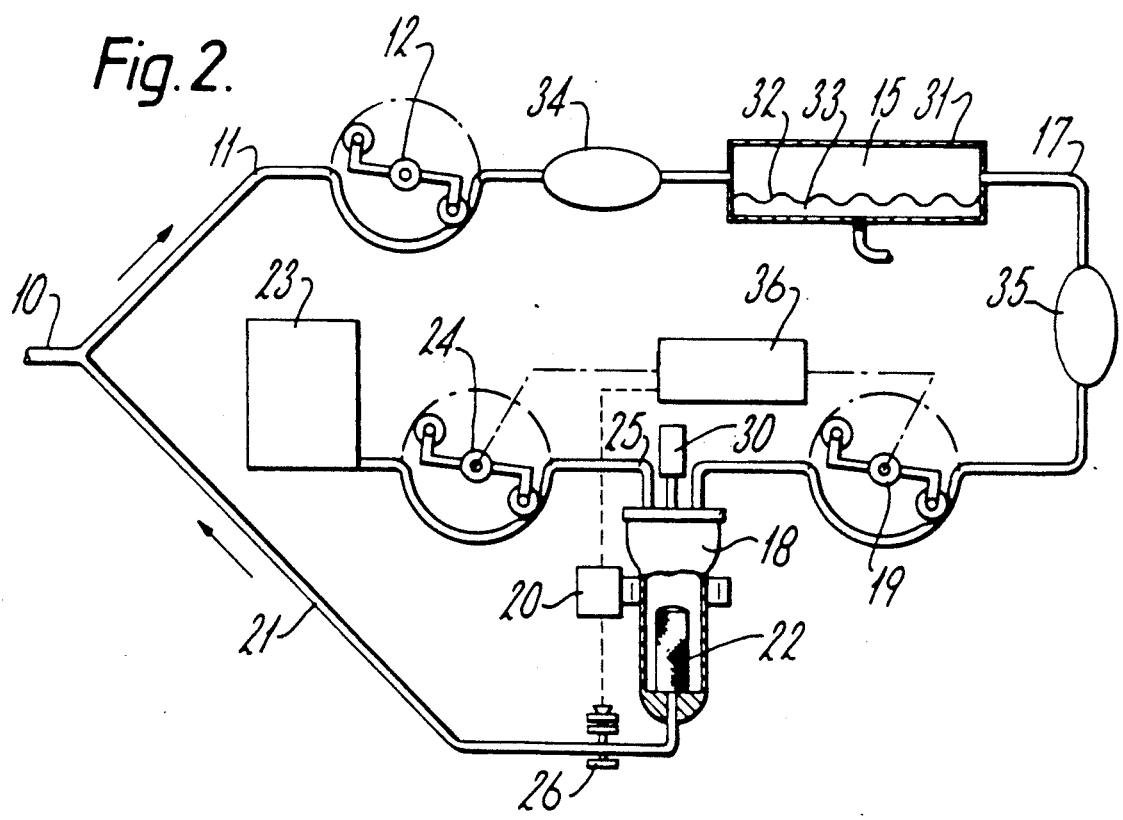
FIG. 2 is a similar view of a second embodiment.

FIG. 2 shows a second embodiment of the artificial kidney according to the invention, in which some arrangements can be used separately or in various combinations with the other embodiments shown.

Thus the perfusion pump 24 and the venous pump 19 are shown as being driven by a common motor 36. They can thus be advantageously driven with rigorous synchronisation at the same instants and at the same speeds or in one and the same speed ratio. This speed ratio can however be adjustable by means of a speed variator of any known type, in order to permit regulation of the ratios of the flow rate of the perfused solution relative to the flow rate of the blood.

The perfusion pump 24 and the venous pump 19 are preferably of the peristaltic type. The peristaltic tubes of the pumps 19 and 24 are advantageously mounted in parallel on one and the same rotor. The coiling diameters of the peristaltic tubes on the rotor, and also the internal and/or external diameters of the peristaltic tubes, are previously determined in relation to the ratio of the average flow rates or of the desired flow rate capacities, in the case of perfusions with a fixed speed ratio.

An obstructive clamping device (not shown) situated for example between the reservoir 23 and the perfusion pump 24 can, if desired, enable the flow of perfused liquid into the blood to be restricted—at least temporarily—without having to modify the motion of the pump 24.

In addition, it is advantageous to provide in the reservoir 23 an empty vessel detector device of a type known per se, not shown, which is capable of effecting, if necessary, the stopping of the perfusion pump 24 to avoid the introduction of air into the blood.

Moreover, the liquids delivered by each of the pumps 19 and 24 flow directly in parallel to the top of the bubble-remover 18 in which their mixing takes place in the desired proportions. It is therefore possible to consider that, in FIG. 2, the perfusion point 25 is situated in proximity to the outlet port of the venous pump 19 which is synchronised with the perfusion pump 24.

FIG. 2 additionally shows, as a blood treatment apparatus, a haemofilter 31 provided with an ultrafiltration membrane 32 separating the apparatus into two compartments 15 and 33, through which pass, respectively, the blood and the ultrafiltrate. This haemofilter is of any known type. When it consists, for example of a bundle of substantially parallel hollow fibres through the interior of which the blood passes, a relatively constant volume is offered to the blood, and this leads to wide variations in the pressure of the blood as a result of the alternate motion of the blood-circulating pumps. It has then been found advantageous to arrange in the blood circuit, for example upstream and downstream of the blood treatment apparatus, one or two pulsation-absorbing devices 34 and 35 of a known type. The flow thus obtained is less haemolysing and more regular, and this is favourable to homogeneous mixing with large quantities of perfusion liquid.

Figure 3:
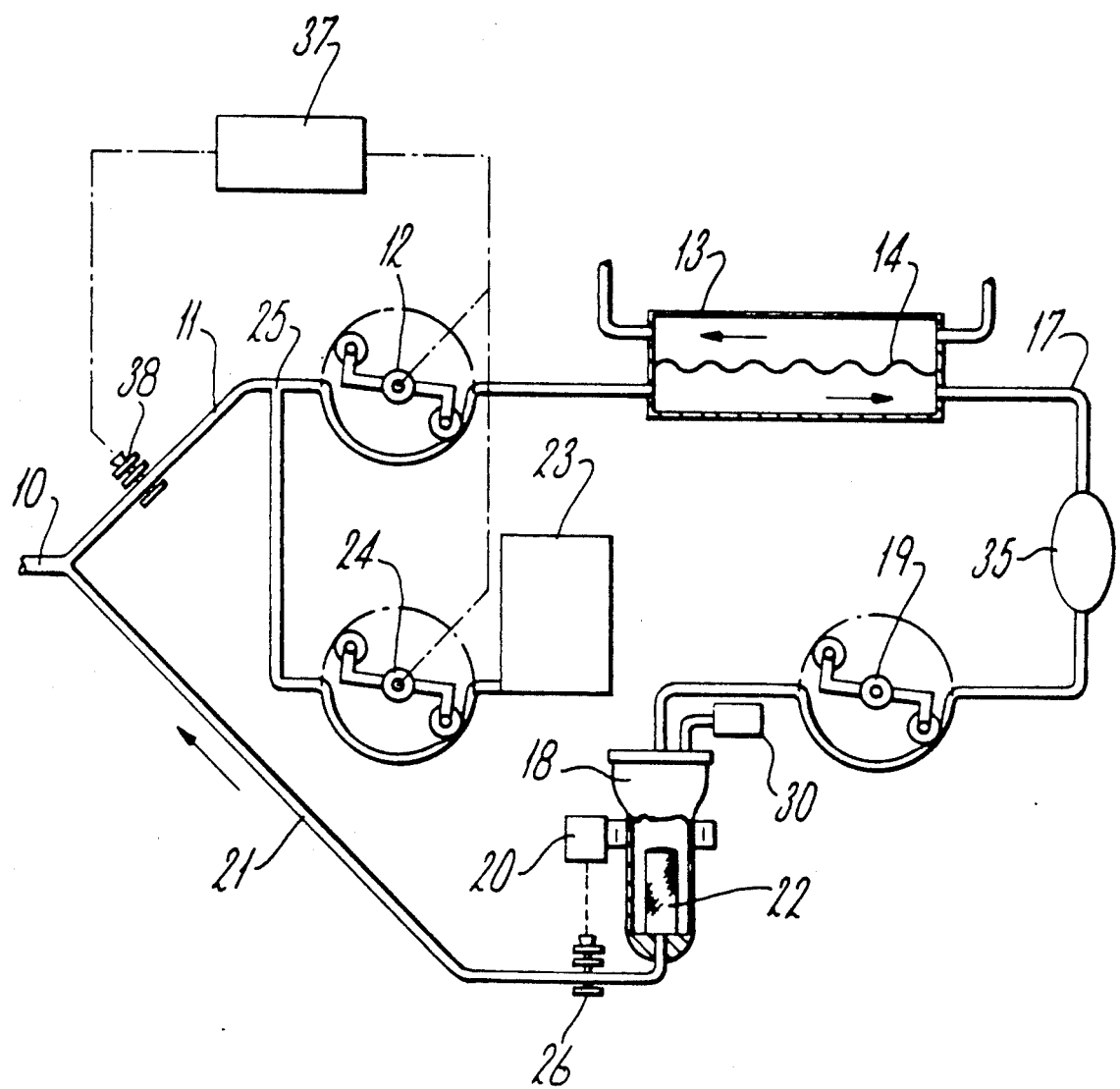
FIG. 3 is a similar view of a third embodiment of artificial kidney according to the invention.

FIG. 3 shows another arrangement, in which an obstructing clamp 38 is situated on the line 11 upstream of the arterial pump 12. The operation of this clamp is so-called automatic, since it is synchronised with that of the pump 12 by way of an electric or electronic control unit 37, so as to avoid erroneously sucking in venous blood from the line 21.

The perfusion point is situated upstream of one of the circulation pumps, for example upstream of the arterial pump 12 and in the immediate proximity of the inlet port of this pump. In addition, the means of actuation of the perfusion pump 24 are under the control of, and preferably synchronised with, the means of actuation of the arterial pump 12, by any known means, for example by way of the control unit 37. Thus, the blood and the perfusion liquid are moved simultaneously and then mixed over the remainder of the extra-corporeal circuit before returning to the patient. However, this arrangement can have the disadvantage that one part of the perfusion liquid leaves the extracorporeal blood circuit shortly after having been introduced into it, by passing through the membrane 14, and this thus constitutes a variant which is not preferred.

The operation of the artificial kidney according to FIG. 3 is sequential. In an initial period, when the venous pump 19 is stopped, the programmer of the unit 37 triggers the opening of the clamp 38 and then the simultaneous rotation of the arterial pump 12 and the perfusion pump 24. When the downstream pressure, measured by a probe (not shown) arranged for example on the pulsation-absorbing device 35 reaches a predetermined maximum value, the programmer 37 stops the pumps 12 and 24 and closes the clamp 38, while during a second period, the venous pump 19 is, in its turn, caused to rotate until the upstream pressure, measured at 35, reaches a minimum predetermined value.

It has generally been found advantageous to actuate the perfusion pump 24 in a discontinuous, periodic manner, with its operation period adjusted to the operation period of one of the two circulation pumps, the arterial or venous pump, and preferably the venous pump. Thus the means of actuation of the pump for perfusing a solution are advantageously synchronised with the means of actuation of one of the two circulation pumps, in particular the venous pump.

If desired, although this is not preferred, it is possible to operate the perfusion pump 24 for a period of time different from that of the venous pump 19. Thus when for example the volumes to be perfused are relatively small, it is possible to actuate the perfusion pump 24 only for a fraction of the time during which the venous pump 19 operates at each period. It is also possible, although this is not preferred, to actuate the perfusion pump 24 once only, whereas the venous pump 19 is actuated two or more times within the same time period.

Conversely, if desired, the operating time of the perfusion pump 24 can exceed overall the operating time of the venous pump 19, for example by a predetermined amount during each period, either by starting early or by stopping late, or by both, relative to the venous pump 19. In these various cases, the corresponding pumps are under mutual control, although they are not completely synchronised.

According to the invention, the motion of the perfusion pump 24, is directly under the control of the motion of at least one of the two circulation pumps 12 or 19. As a result of this, it is also under the control of the position of the upstream or downstream clamps, such as 38 or 26, generally indirectly. The perfusion pump 24 preferably only operates when the corresponding clamp 38 or 26, closes to the perfusion point 25, is open.

The invention permits the perfusion of all types of physiological liquids or sterile solutions, previously proportioned in accordance with the needs of the patient. It is thus possible to correct requirements of inorganic salts, proteins and the like.

Several solutions can also be injected successively or simultaneously, for example in parallel, in determined or independent proportions by means of several reservoirs 23 and/or pumps 24. In addition, it is of course possible to inject heparin independently upstream in the extracorporeal blood circuit, as is a well known practice.

The sequential control of the means of perfusion can of course be varied in any suitable manner to suit particular requirements.

We claim:

1. An artificial kidney comprising an extracorporeal blood circuit including:
   (a) a blood treatment apparatus having a selectively permeable membrane;
   (b) a single needle connectable to a patient's arterial-venous network;
   (c) a first pump having an inlet port connected to said needle and an outlet port connected to said blood treatment apparatus;

(d) a second pump having an inlet port connected to said blood treatment apparatus and an outlet port connected to said needle;

(e) first and second actuating means for causing the operation of said first and second pumps, respectively;

(f) at least one reservoir for at least one solution to be introduced into said extracorporeal blood circuit;

(g) at least one perfusion pump having an inlet port connected to said reservoir and an outlet port connected to said extracorporeal blood circuit;

(h) third actuating means for causing the operation of said perfusion pump; and (i) means connecting said third actuating means with one of the first and second actuating means, whereby the operation of the perfusion is synchronized with one of said first and second pumps.

2. An artificial kidney as claimed in claim 1, wherein the outlet port of said perfusion pump is connected to said extracorporeal blood circuit at a point in proximity to the inlet or outlet port of the circulation pump of which the actuating means is connected to said third actuating means.

3. An artificial kidney as claimed in claim 1, wherein said third actuating means is controlled by said second actuating means.

4. An artificial kidney as claimed in claim 1, wherein said third actuating means are synchronised with one of said first and second actuating means in an adjustable speed ratio.

5. An artificial kidney as claimed in claim 1, wherein said third actuating means and the one of said first and second actuating means with which it is synchronized are controlled by a common motor.

6. An artificial kidney as claimed in claim 1, wherein said perfusion pump and said one of the first and second pumps of which the actuating means is controlled with the third actuating means are both of the peristaltic type, having peristaltic tubes.

7. An artificial kidney as claimed in claim 6, wherein said perfusion pump and the one of said first and second pumps of which the actuating means is controlled with said third actuating means have a common rotor which simultaneously actuates the two peristaltic tubes of said pumps, which are mounted in parallel on said rotor.

8. An artificial kidney as claimed in claim 1, and further comprising a closing device for the extracorporeal blood circuit situated between said outlet port of said second pump and said needle and downstream of any other operating part of the extracorporeal blood circuit.

9. An artificial kidney as claimed in claim 8, and further comprising means to control said closing device synchronised with at least one of said actuating means.

* * * * *